(12) United States Patent
Pollack (10) Patent No.: US 7,276,236 B2
(45) Date of Patent: Oct. 2, 2007

(54) METHODS OF PREPARING IMMUNE GLOBIN AND USES THEREOF

(75) Inventor: William Pollack, Oceanside, CA (US)

(73) Assignee: Atopix Pharmaceuticals Corporation, Carlsbad, CA (US)

(*) Notice: Subject to any disclaimer, the term of this patent is extended or adjusted under 35 U.S.C. 154(b) by 0 days.

(21) Appl. No.: 09/952,778

(22) Filed: Sep. 13, 2001

(65) Prior Publication Data

US 2002/0064526 A1    May 30, 2002

Related U.S. Application Data

(63) Continuation-in-part of application No. 09/660,862, filed on Sep. 13, 2000.

(51) Int. Cl.
| | |
|---|---|
| A61K 39/395 | (2006.01) |
| A61K 39/00 | (2006.01) |
| A61K 35/64 | (2006.01) |
| A61K 38/00 | (2006.01) |
| A61K 38/28 | (2006.01) |

(52) U.S. Cl. ............... 424/130.1; 424/133.1; 424/134.1; 424/538; 424/539; 514/2; 514/4

(58) Field of Classification Search ............... 424/85, 424/130.1, 184, 804, 539; 530/387.1, 389.4, 530/413, 412, 387, 362; 435/7.1; 425/7.9

See application file for complete search history.

(56) References Cited

U.S. PATENT DOCUMENTS

| | | | |
|---|---|---|---|
| 4,089,944 A | 5/1978 | Thomas | |
| 4,186,192 A | 1/1980 | Lundblad et al. | |
| 4,322,403 A | 3/1982 | Bunnig | |
| 4,436,724 A | 3/1984 | Ohnishi | |
| 4,482,483 A | 11/1984 | Curry et al. | |
| 4,597,966 A | 7/1986 | Zolton et al. | |
| 4,639,513 A | 1/1987 | Hou | |
| 4,719,290 A | 1/1988 | Curry et al. | |
| 5,177,194 A | 1/1993 | Sarno et al. | |
| 5,346,687 A | 9/1994 | Rhodes | |
| 5,489,519 A * | 2/1996 | Deeley et al. | 435/69.1 |
| 5,563,120 A | 10/1996 | Kuznetsov | |
| 5,908,827 A | 6/1999 | Sirna | |
| 6,069,236 A | 5/2000 | Burnouf-Radosevich et al. | |
| 6,281,336 B1 * | 8/2001 | Laursen et al. | 530/390.1 |

FOREIGN PATENT DOCUMENTS

EP    0205352 A2    6/1986

OTHER PUBLICATIONS

Schumacher et al, Am J of Trop Med Hyg, 55(2), 1996, 197-201.*
Nai-Kong et al, Annals of Allergy, vol. 50, Mar. 1983.*
Hoffman et al, Annals of Allergy, 1991, 46/1, 17-23.*
Bird et al, Journal of Immunological Methods, 71, 1984, 97-105.*
Aalberse et al, The Journal of Immunology, vol. 130, No. 2, Feb. 1993.*
Urbanek et al, Clinical Allergy, vol. 16, pp. 317-322.*
Lessof et al, The Johns Hopkins Medical Journal, Vo. 142, No. 1, Jan. 1978.*
Lessof et al, Monogr. Allergy, vol. 12, pp. 253-256.*
Urbanek et al, Clinical Allergy, 1986, vol. 16, pp. 317-322.*
Aalberse et al, Journal of Immunology, vol. 130, 1993.*
Urbanek et al (Clinical Allergy, vol. 16, pp. 317-322).*
Lessof et al (Monogr. Allergy, vol. 12, pp. 253-256).*
Aalberse, et al. "Serologic Aspecs of IgG4 Antibodies", *J. of Immunol.* 130(2): 722-723 (Feb. 1983).
BOUSQUET "Combination of Passive and Active Immunization in Honeybee Venom Immunotherapy", *Journal of Allergy and Clinical Immunology* vol. 79:6 pp. 947-954 (abstract).
Cheung, et al. "Honey Bee Venom Specific Immunoglobulin G4 in Honey Bee String allergic Patients and Bee Keepers," *Anls. Allergy* 50:155-160 (Mar. 1983).
B.E., Garcia, "Blocking Effect on the Release of Antigen-Specific Histamine," *Journal of Invetigational Allergology Clinical Immunolgy* vol. 3:1 pp. 26-33, Jan.-Feb., 1993 (Abstract).
Lessof, et al. "Effects of Passive Antibody in Bee Venom Anaphylaxis" *The Johns Hopkins Med. J.* vol. 142: 1-7 (Jan. 1978).
Lessof, et al. "Protection Against Anaphylaxis in Hymenoptera-Sensitive Patietns by Passive Immunization" *Monogr. Allergy* 12:253-256 (Karger, Basel 1977).
Schumacher, et al. "Neutralization of Bee Venom Lethality by Immune Serum Antibodies," *Am. J. Trop. Med. Hyg.* 55(2): 197-201 (1996).
Urbanek, eta l. "Sub-class of IgG anti-bee venom antibody produced during bee venom immunotherapy and its relationship to long-term protection from bee stings and following termination of venom immunotherapy" *Clin. Allergy* 16:317-322 (1986).
Bird, P. et al. "The Separation of Human Serum IgG into Subclass Fractions by Immunoaffinity Chromatography and Assessment of Specific Antibody Activity," *J. of Immunological Methods* 1984, pp. 97-105, vol. 71.
Lambin, P. et al. "Purification of Human IgG4 Subclass with Allergen-Specific Blocking Activity," *J. of Immunological Methods* 1993, pp. 99-111, vol. 165.
Persson, M.A.A. "Preparation of Human Sera Containing One Single IgG Subclass Using Affintiy Chromatography," *J. of Immunological Methods* 1987, pp. 91-98, vol. 98.
Van Toorenebergen et al. "IgG4 and Passive Sensitization of Basophil Leukocytes," *Int. Archs Allergy Appl. Immun.* 1981, pp. 432-440, vol. 65.

* cited by examiner

*Primary Examiner*—Nita Minnifield
*Assistant Examiner*—Vanessa L. Ford
(74) *Attorney, Agent, or Firm*—Townsend and Townsend and Crew LLP (57) ABSTRACT

The present invention provides for methods of preparing purified immune globulins, immune globulin compositions, and methods of treating allergies and conditions by administering immune globulin compositions. For example, the present invention provides for purified IgG4 that is essentially free of other IgG subtypes that can be used to treat allergies and other conditions.

14 Claims, 2 Drawing Sheets

METHODS OF PREPARING IMMUNE GLOBIN AND USES THEREOF

CROSS-REFERENCES TO RELATED APPLICATIONS

This application is a continuation-in-part and claims the benefit of U.S. patent application Ser. No. 09/660,862, filed on Sep. 13, 2000, the teachings of which are herein incorporated by reference.

STATEMENT AS TO RIGHTS TO INVENTIONS MADE UNDER FEDERALLY SPONSORED RESEARCH AND DEVELOPMENT

Not Applicable.

BACKGROUND OF THE INVENTION

At present, the only treatment for serious insect sting allergies, seasonal allergies and year-round allergies is desensitization (hyposensitization) by an allergist. However, this treatment is expensive, sometimes dangerous, inefficient, painful and frequently ineffective, costing as much as $4,000.00 per year. On average, therapy continues every 2-3 weeks for 3-5 years, resulting in a high dropout rate. In addition, severely sting-allergic individuals must rely on emergency adrenaline and cortisone kits, such as Epipen® (Dey Laboratories, Napa, Calif.), which in many cases are not available at the moment of need. Antihistamines do provide temporary relief from mild allergy symptoms, though often with undesirable side effects and do not prevent anaphylactic shock in severely allergic individuals.

Compositions containing IgG preparations have been used to prevent or control reactions to allergens and antigens. Immune globulin or immunoglobulin are commonly obtained from pooled plasma samples from donors, and typically contains IgG antibodies to various bacterial and viral infectious agents, making it useful for prophylaxis and treatment of disease, particularly in patients with compromised immune systems that make them susceptible to infections. Patients with normal immune systems may also require IgG antibodies in order to overcome certain infections that currently cannot be effectively treated with antibiotics. Many uncommon bacterial infections and viral infections against which patients may have no normal immunity can be treated by administration of immune globulins.

Hyper-immune serum globulin is obtained from plasma from donors selected for high titers (antibody concentrations) of specific antibodies, and has been used to prevent hepatitis B, tetanus, rabies, and varicella-zoster as well as to prevent immunization to the Rh-factor in Rh-negative mothers. Individuals who have recovered from bacterial illnesses typically develop antibodies that can confer immunity in others to the illness. For example, the Rh Immune Globulin (RhoGam®) (Ortho-Clinical Diagnostics, Inc., Raritan, N.J.) has been used to inject into Rh negative mothers to prevent hemolytic disease in their Rh positive fetuses. Also, Medimmune produces Immune Globulin to prevent/treat respiratory syncytial disease virus infections of young children. Immune Globulin preparations such as H-Big™ (NABI) has been used to prevent hepatitis B infection.

In addition, IgG preparations from beekeepers that contain all the IgG subtypes have been used for the treatment of individuals who are sensitive to bee stings (see e.g., Schumacher et al. (1996) *Am. J Trop. Med. Hyg.* 55(2): 197-201; Lessof et al. (1978) *Johns Hopkins Med. J.* 142(1): 1-7; and Lessof et al. (1977) *Monogr. Allergy* 12: 253-256).

Similarly, antitoxins have been shown to be of great value in treating patients envenomated by bacterial toxins or from the bites of venomous snakes or stings of insects. Such antivenins were mostly derived from the serum of immunized horses, but are today almost exclusively obtained from the plasma of immune donors from which the antibody or antibodies are removed. Such antibodies occur in the gamma globulin. A small portion of the population is extremely sensitive (allergic) to the stings of flying insects, especially honey bees, wasps, hornets and yellow jackets (the hymenoptera). The advance of aggressive Africanized or so-called "killer" bees has also increased risks for the general population from multiple bee stings and especially for individuals highly allergic to bee venom. In view of these risks, it is desirable to provide a relatively inexpensive method for manufacturing immune globulins that can provide protection against serious life threatening allergic reactions such as anaphylaxis and/or can be used as an antitoxin to neutralize the toxic properties of the venoms and prevent "end organ" damage, thus possibly saving the life of the victim of the stings. Intravenous administration of immune globulin allows the desired level of circulating antibody to be reached quickly.

Recently, it has been recognized that the IgG4 content is increased in persons exposed to certain allergens. For example, the IgG4 subtype is increased in individuals that have been exposed to bee venom (Aalberse et al. (1983) *J. Immunol.* 130(2):722-726; Cheung et al. (1983)*Ann. Allergy* 50(3):155-160; Urbanek et al. (1986) *Clin. Allergy*16(4): 317-322). In many cases, exposure to an antigen or allergen results in an IgG4 restricted response (see, e.g., Aalberse et al. (1983) *J. Immunol.* 130(2):722-726). For example, exposure to antigens such as grass pollen and honey bee pollen results in IgG antibodies that are predominantly of the IgG4 subclass.

Methods for preparing IgG compositions are known in the art (see, e.g., U.S. Pat. Nos. 6,069,236, 4,719,290, 4,482,483,and 5,177,194). However, no one to date has prepared compositions that comprise IgG4 that is substantially free from other IgG subtypes (e.g., IgG1, IgG2, and IgG3). Such a preparation would have the advantage of containing less protein and a higher amount of blocking antibody (e.g., IgG4) per unit weight or per unit of protein that is being injected. Furthermore, intravenous injections of many immune globulin products can lead to reactions that are caused by aggregation and fragmentation of the immune globulin which forms during the fractionation and preparation of the product. It is desirable, therefore, to provide a method of manufacture of immune globulins that is safe and effective, meeting current standards for sterility and pyrogenicity. Thus, a need in the art exists for IgG4 compositions that are substantially free from other IgG subtypes that can be used in the acute or prophylactic treatment of diseases and conditions. The present invention fulfill these and other needs in the art.

BRIEF SUMMARY OF THE INVENTION

This invention provides methods and compositions that relate to purified immune globulins that are useful for the treatment of diseases and conditions. In one aspect, the present invention provides methods of preparing purified IgG subtypes that are essentially free of other IgG subtypes. For example, the present invention provides methods of preparing IgG that is essentially free of other IgG subtypes that comprises the steps of: (a) adjusting a clarified plasma to a pH of about 6.4 to about 6.6 and a conductivity of between about 3.5 to about 6 millisiemens; (b) contacting the plasma obtained from step (a) with an anion exchange resin to obtain a first fraction that does not bind to the anion exchange resin; and (c) contacting the first fraction of step (b) with a cation exchange resin to obtain a second fraction that does not bind to the cation exchange resin, wherein the second fraction comprises IgG4 that is essentially free of other IgG subtypes. In certain embodiments, the anion exchange resin comprises DEAE groups. In other embodiments, the cation exchange resin comprises carboxymethyl groups. In still other embodiments, these methods can further comprise the steps of: (d) adding NaCl to a final concentration of about 0.03 to about 0.05 M NaCl; (e) filtering the solution of step (d); (f) centrifuging the filtrate of step (e); (g) freezing the supernatant of step (f); (h) thawing the frozen supernatant of step (g); (i) adding a monosaccharide or disaccharide to the thawed supernatant of step (h) to a final osmolarity of between about 0.22 to about 0.35 OsM; (j) filtering the solution of step (i); (k) freezing the filtered solution of step (j); (l) thawing the frozen solution of step (k); and (m) lyophilizing the solution of step (l).

In another aspect of the invention, the purified IgG4 can be used in methods of treating a patient envenomated by an insect sting. Typically, these methods comprise administering a pharmaceutical composition comprising a therapeutic amount of IgG4 that is essentially free of other IgG subtypes to a patient envenomated by an insect sting. The insects can be selected from a wide variety of insects that include, but are not limited to, flying insects, bees, honey bees, Africanized "killer" bees, wasps, hornets, yellow jackets, and hymenoptera. In certain embodiments, it is desired to also administer epinephrine or an anti-histamine drug. The pharmaceutical compositions can be administered prior to or after the patient has been envenomated. In certain embodiments, the IgG4 is prepared using a method that comprises: (a) adjusting a clarified plasma to a pH of about 6.4 to about 6.6 and a conductivity of between about 3.5 to about 6 millisiemens; (b) contacting the plasma obtained from step (a) with an anion exchange resin to obtain a first fraction that does not bind to the anion exchange resin; and (c) contacting the first fraction of step (b) with a cation exchange resin to obtain a second fraction that does not bind to the cation exchange resin, wherein the second fraction comprises IgG4 that is essentially free of other IgG subtypes.

In another aspect, the present invention provides for methods of desensitizing a patient to venom (e.g., insect sting venom) comprising: administering a pharmaceutical composition comprising a therapeutic amount of IgG4 that is essentially free of other IgG subtypes to a patient envenomated by an insect sting; and subsequently administering a desensitizing amount of insect sting venom to the patient. In certain embodiments, the IgG4 is prepared using a purification method comprising the steps of: (a) adjusting a clarified plasma to a pH of about 6.4 to about 6.6 and a conductivity of between about 3.5 to about 6 millisiemens; (b) contacting the plasma obtained from step (a) with an anion exchange resin to obtain a first fraction that does not bind to the anion exchange resin; and (c) contacting the first fraction of step (b) with a cation exchange resin to obtain a second fraction that does not bind to the cation exchange resin, wherein the second fraction comprises IgG4 that is essentially free of other IgG subtypes.

In still another aspect, the present invention provides for methods of decreasing the severity of an allergic response to an allergen comprising: administering a pharmaceutical composition comprising a therapeutic amount of IgG4 that is essentially free of other IgG subtypes to a patient in need thereof. Typically, the IgG4 is essentially free of IgG1, IgG2, and IgG3.

In yet another aspect, the present invention provides for pharmaceutical compositions comprising IgG4 that is essentially free of other IgG subtypes. In certain embodiments, IgG4 of said composition is prepared using a method comprising the steps of: (a) adjusting a clarified plasma to a pH of about 6.4 to about 6.6 and a conductivity of between about 3.5 to about 6 millisiemens; (b) contacting the plasma obtained from step (a) with an anion exchange resin to obtain a first fraction that does not bind to the anion exchange resin; and (c) contacting the first fraction of step (b) with a cation exchange resin to obtain a second fraction that does not bind to the cation exchange resin, wherein the second fraction comprises IgG4 that is essentially free of other IgG subtypes.

In still yet another aspect, the present invention provides for pharmaceutical compositions that comprises IgG1 and IgG4, and are essentially free of other IgG subtypes.

These and other aspects will become more apparent when read with the accompanying Figures and detailed description which follows.

DEFINITIONS

An "allergen" is any substance that causes an allergy.

An "allergy" is an inappropriate and harmful response of the immune system to normally harmless substances.

"Anaphylactic shock" is a life-threatening allergic reaction characterized by a swelling of body tissue including the throat, difficulty in breathing and a sudden fall in blood pressure.

"Antibody" refers to a polypeptide substantially encoded by at least one immunoglobulin gene or fragments of at least one immunoglobulin gene, that can participate in specific binding with a ligand. The term includes naturally-occurring forms, as well as fragments and derivatives. Fragments within the scope of the term as used herein include those produced by digestion with various peptidases, such as Fab, Fab' and F(ab)'2 fragments, those produced by chemical dissociation, by chemical cleavage, and recombinantly, so long as the fragment remains capable of specific binding to a target molecule. Typical recombinant fragments, as are produced, e.g., by phage display, include single chain Fab and scFv ("single chain variable region") fragments. Derivatives within the scope of the term include antibodies (or fragments thereof) that have been modified in sequence, but remain capable of specific binding to a target molecule, including interspecies chimeric and humanized antibodies. As used herein, antibodies can be produced by any known technique, including harvest from cell culture of native B lymphocytes, hybridomas, recombinant expression systems, by phage display, or the like.

Antibodies can be a polyclonal mixture or monoclonal. An "antibody" can be derived from sequence of a mammal, non-mammal (e.g., birds, chickens, fish, etc.), or fully synthetic antibody sequences. A "mammal" is a member of the class Mammalia. Examples of mammals include, without limitation, humans, primates, chimpanzees, rodents, mice, rats, rabbits, sheep, and cows. The term "antibody" also refers to fragments and substitutes for antibodies such as F(ab')$_2$, Fab', and Fab fragments.

Methods of production of polyclonal antibodies are known to those of skill in the art. In brief, an immunogen, preferably a purified protein or biomolecule, is mixed with an adjuvant and animals are immunized. When appropriately high titers of antibody to the immunogen are obtained, blood is collected from the animal and antiserum is prepared.

Monoclonal antibodies may be obtained by various techniques familiar to those skilled in the art. Briefly, spleen cells from an animal immunized with a desired antigen are immortalized, commonly by fusion with a myeloma cell (see Kohler & Milstein, *Eur. J Immunol.* 6:511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host.

"Antigen" refers to a ligand that can be bound by an antibody. An antigen need not be immunogenic. The portions of the antigen that make contact with the antibody are denominated "epitopes".

A "blocking-antibody" is an antibody that competitively inhibits allergen from cross-linking IgE on the surface of the mast cell and circulating basophils. Blocking-antibody is found in the IgG class of immunoglobulins when an allergic individual becomes desensitized to an allergen. Blocking-antibody occurs as IgG1 and IgG4.Greater concentrations are found in the IgG4 subtype in individuals who become completely immune to the allergen. For example, in beekeepers, who show no adverse reactions to daily multiple stings, the blocking-antibody to bee-venom occupies up to 80% of the IgG4.

The term "hymenoptera" refers to an order of poisonous flying and stinging insects. Members of this group include, but are not limited to, bees, wasps, hornets, fire ants and the like.

A sample comprises IgG4 that is "essentially free of other IgG subtypes" when IgG1, IgG2, and IgG3 are each less than 3% (w/v) of the total amount of IgG that is present. The respective percentages of IgG1, IgG2, IgG3, and IgG4 can be determined using methods known to those skilled in the art including, without limitation, immunological detection methods, densitometric scans of stained polyacrylamide gels, mass spectrometry methods, and amino acid sequencing.

A sample comprises IgG1 that is "essentially free of other IgG subtypes" when IgG2, IgG3, and IgG4 are each less than 3% (w/v) of the total amount of IgG that is present. The respective percentages of IgG1, IgG2, IgG3, and IgG4 can be determined using methods known to those skilled in the art including, without limitation, immunological detection methods, densitometric scans of stained polyacrylamide gels, mass spectrometry methods, and amino acid sequencing.

A sample comprises IgG2 that is "essentially free of other IgG subtypes" when IgG1, IgG3, and IgG4 are each less than 3% (w/v) of the total amount of IgG that is present. The respective percentages of IgG1, IgG2, IgG3, and IgG4 can be determined using methods known to those skilled in the art including, without limitation, immunological detection methods, densitometric scans of stained polyacrylamide gels, mass spectrometry methods, and amino acid sequencing.

A sample comprises IgG3 that is "essentially free of other IgG subtypes" when IgG1, IgG2, and IgG4 are each less than 3% (w/v) of the total amount of IgG that is present. The respective percentages of IgG1, IgG2, IgG3, and IgG4 can be determined using methods known to those skilled in the art including, without limitation, immunological detection methods, densitometric scans of stained polyacrylamide gels, mass spectrometry methods, and amino acid sequencing.

A sample comprises "IgG1 and IgG4, and is essentially free of other IgG subtypes" when IgG2 and IgG3 are each less than 3% (w/v) of the total amount of IgG that is present. The respective percentages of IgG1, IgG2, IgG3, and IgG4 can be determined using methods known to those skilled in the art including, without limitation, immunological detection methods, densitometric scans of stained polyacrylamide gels, mass spectrometry methods, and amino acid sequencing.

The phrase "clarified plasma" refers to a plasma sample that has been subjected to a process such as centrifugation or filtration to reduce or eliminate cells or cellular debris.

An "immune donor" is a subject that contains a blocking antibody against an allergen or antigen.

A "desensitizing amount of insect sting venom" is that amount of insect sting venom that is sufficient to achieve desensitization when administered after an administration of blocking antibody (i.e., IgG1, IgG4,etc.) to a patient.

DETAILED DESCRIPTION

I. Introduction

This invention provides for purified immune globulins and methods for preparing purified immune globulins. These purified immune globulins are useful for the prevention and treatment of adverse reactions to antigens and allergens. In particular, methods for preparing IgG4 that is essentially free from other IgG4 subtypes are provided. Advantageously, the present invention provides a method to prepare IgG4 that is essentially free of other IgG subclasses for administration to subjects that are in need thereof.

In one embodiment, the present invention provides a method to selectively purify IgG4 and/or IgG1 away from the other IgGs. The present invention provides methods for preparing such IgG4 and other immune globulin preparations (e.g., IgG1, IgG2, IgG3IgA, IgM, monoclonal antibodies, Fabs, Fv's, etc.) that can be used as blocking antibodies for methods of treating diseases and conditions.

II. Methods for Preparing Immune Globulins

In certain aspects, the present invention provides methods for preparing immune globulins that are useful as blocking antibodies, which in certain aspects involves purifying one or more types or subtypes of antibodies. Briefly, the methods involve the use of anion and cation exchange resins to purify the desired immune globulins from a particular source.

Sources of Immune Globulins

The immune globulins can be purified from a variety of sources, such as animals, humans, bacteria, plants, yeast. The source contains the immune globulin(s) that are useful as a blocking antibody. In certain cases, the source is a human or animal source that has been previously exposed to an antigen or allergen of choice, e.g., an immune donor. These sources can be exposed on purpose by administering the antigen to the subject (e.g., by injection). Alternatively, the source can be a subject that has been or is exposed to the antigen such as Ragweed, Spring allergens, House Allergens, bee venom, stinging insect venom, reptile venom, etc. In the case of ragweed, the immune donors can be immunized with ragweed extract (Ragweed E). Similarly, immune donors for can be injected with Spring Allergens (i.e., perennial grasses such as Timothy Grass, Bermuda Grass, Sage, and tree pollens, etc.) and House Allergens (i.e., animal dander, cat saliva, and house dust mite feces, etc.).

Polyclonal, monoclonal antibodies as well as other antibodies (e.g., Fv, antibody fragments, Fab, etc) can be purified using the present invention. For example, mAbs can be purified from essentially any source that can express a mAb such as an animal cell, a yeast cell, a bacterium, a plant cell, a plant (see, e.g., U.S. Pat. No. 5,959,177) and the like.

Typically, the source of the immune globulins is subjected to one or more clarification steps to remove large particles, and insoluble material. The clarification steps include, centrifugation, filtration, and decanting, as well as other clarification methodologies known to those of skill in the art. The clarified or unclarified immune globulin source is applied to an anion exchange format.

Anion Exchange Step

In certain aspects, the source of the antibodies (clarified or unclarified) is adjusted to a pH of between 6.2 to 6.7. Preferably, the source of the antibodies is plasma and the resultant pH is 6.5. The conductivity of the solution is adjusted as well to a between about 3.5 to about 6 millisiemens. The optimal pH and conductivity will depend on such factors as the source of the antibodies, the buffer (if any) being used, the salt concentration, and the exchange resin being used. The pH and conductivity adjusted solution is then contacted with an anion exchange resin. Many anion exchange resins are known in the art and include, without limitation, resins that contain groups such as DEAE (diethylaminoethyl), QAE (diethyl-(2-hydroxylpropyl)aminoethyl; quaternary amino ethyl), TEAE (triethylaminoethyl), etc. These groups are typically attached to a solid support such as Sepharose®, cellulose, agarose, etc.

The contacting can be carried out in batch and/or a column format. The immune globulins do not preferentially adsorb to the anion exchange resin and the majority of the desired immune globulin(s) are still in solution. After a suitable period of time, the unbound immune globulins are then separated from the exchange resin. In the case of a column format, the immune globulins will be found in an effluent peak (e.g., in the flow-through fractions). For a batch format, the resin can be filtered away from the unbound immune globulins. Many other methods for separating the resin from the immune globulins that are free in solution are known in the art (e.g., centrifugation, decanting, etc.).

Cation Exchange Step

The immune globulins from the anion exchange step are then contacted with a cation exchange resin. Many different cation exchange resins are known in the art and are commercially available. The cation exchange groups are typically attached to the same or similar solid supports (e.g., resins, etc.) discussed herein for anion exchange groups. Examples of suitable cation exchange groups include, but are not limited to, carboxymethyl (CM), phospho, and sulphopropyl (SP) groups. As with the anion exchange step described above, this step can be carried out in batch and/or column format. In certain embodiments, when the pH of the buffer is equal to or higher than the pI of the antibody or antibodies of interest (e.g., IgG4, IgG1, IgG2, IgG3, IgA, IgM, mAbs, etc), the antibodies being purified do not preferentially adsorb to the cation exchange resin and the majority of the desired antibody remains in solution. In the case of a column format, for example, the IgG4 (or other blocking antibody being purified) is found in the flow-through fractions when the pH is between 6.4 to 6.6, preferably at a pH of 6.5.

The pH of the cation exchange material will depend on the isoelectric point of the antibody being purified. The immune globulin being purified will typically elute at a pH that is at or more basic than the pI of the immune globulin being purified. For example, in certain embodiments, IgG4 that is essentially free from other IgG subtypes is purified on a CM-Sephadex® column that is equilibrated using a buffer that preferably has a pH of between 6.4 to 6.6, and more preferably has a pH of 6.5. In certain embodiments, a shallow pH gradient can be used to elute a particular antibody, such as IgG1, IgG2, IgG3,or IgG4. Using the methods of the present invention, IgG1 and IgG4 can be purified to homogeneity. These preparations typically contain much protein aggregates and degraded protein than methods such as the Cohn method (see U.S. Pat. No. 2,390,074; and Cohn et al., (1946) *JACS* 68:459-475, 1946).

Exemplary Embodiment of the Invention

In certain embodiments, IgG4 is purified from plasma by the following method. First, a pool of donor plasma is first assembled, typically from donors who already have hyper immune serum globulin against the desired antigen(s) or allergen(s). An aliquot pool of the plasma units is made typically to equal about 10 ml, prior to pooling, based on the original volumes or weights of the plasma bags. In preferred embodiments, the plasma is treated to reduce or eliminate any viral contamination with a virucide or viral filter.

It is useful to determine the total IgG content of the aliquot pool, the total IgG4 of the aliquot pool, the total antibody in the aliquot pool, and the proportion or percentage of blocking antibody in the IgG4 fraction in the aliquot pool to several antigens in the venom. The determination of the total IgG of the aliquot pool is preferably performed by a sensitive technique for detecting and measuring antibodies in a solution, such as an enzyme-linked immunosorbent assay (ELISA) method, and/or Radial Immune Diffusion (RID) method, whichever gives the most reproducible and accurate data against known standards. The total IgG4 of the aliquot pool can also be determined similarly by ELISA or RID methods. The total antibody can similarly be determined either by ELISA, or a radioimmunoassay (RIA) or RAST tests, providing the latter can be standardized for true quantitative determinations of specific antibodies.

An acceptable alternative is the determination of the ratio of diffusion of the IgG and IgG4 in RID plates. The purpose of this analysis is to compare the final IgG4 preparation in order to estimate losses and costs of production. These tests are useful because IgG4 offers a unique ability to provide blocking antibody with known freedom from any ability of the antibody to bind to mast cells and basophiles, unlike IgG1, IgG2 and IgG3, which have low affinity receptors for these important allergy mediator cells. Purified IgG4 blocking antibody that is essentially free of IgG1, IgG2, or IgG3 has not been used before for this purpose.

These same series of tests can be used throughout the purification process and to estimate the dosage and vialing requirements and to estimate the costs of manufacturing. Other tests can be performed on the plasma, samples from the purification process, on the pharmaceutical compositions, etc. These tests are typical tests which are part of really current Good Manufacturing Practices (cGMP). These tests include, without limitation: a) acute toxicology in two rodents; b) pyrogen tests by the Limulus method; c) sterility tests after sterile filtration and before vialing and lyophilization; d) total protein by Kjeldahl or other suitable methods; e) protein electrophoresis; f) total purity analysis for any contaminating proteins or other impurities; g) gel filtration for determination of split products or polymers; h) analysis for viral contaminants, e.g. HIV, HBV, HCV etc. by the most sensitive methods, extant; and i) other tests required by the FDA and in the Federal Register.

Following testing of the donor plasma pool, the donor plasma pool is typically frozen for storage until it is time for further processing of the donor plasma pool. The plasma units selected from prior antibody analysis (usually 600 to 800 milliliters each), that are to constitute the final plasma pool to be fractionated, are removed from the freezer and allowed to thaw at approximately 5° C.

The plasma units are then pooled into a sterile container under aseptic conditions in a class 100 or less clean room or laboratory air-flow containment area. The weight of the plasma pool is then measured to obtain the total volume.

The plasma should be treated in accordance with a virucidal method, such as the "solvent-detergent" method of the New York Blood Bank, by pasteurization, or by viral filtraction. Whatever method is used to sterilize the plasma pool, the plasma is typically treated to make it comparable to the original plasma in terms of its suitability for fractionation by the method to be described. For example, it is preferred that the final post-sterilized pool have the same pH and ionic strength (as judged by conductivity measurements) as the original pre-sterilized pool of plasma.

In certain embodiments, the sterilized plasma pool is then treated by adding approximately 7 grams of microcrystalline silica (Aerosil 200) per liter of the pool. The Aerosil is previously sterilized at about 180°-185° C. for at least 4 hours in a hot air oven. The addition of the Aerosil to the plasma should be done aseptically. The plasma should then be stirred slowly (so as not to create foaming) for about 1 hour at room temperature under aseptic conditions.

The suspension is then clarified. Typically, the suspension is centrifuged at about 3000×g for about 30 minutes at 2-8° C. or by filtering. The supernate or filtrate is then carefully decanted into a large sterile and depyrogenated container. To recover additional material, the Aerosil can be resuspended in a volume, equivalent to 14% of the starting volume of the plasma, of pyrogen-free 0.9% sodium chloride solution. After mixing, the suspension is centrifuged at about 3000×g for 30 minutes at 2-8° C., maintaining sterility throughout the procedure. The supernates are then combined and the plasma pool is clarified by passage of the plasma pool through a sterile Millipore AW 19 pre-filter, or equivalent membrane. The conductivity of a small sample of the filtered pool should then be determined and the bulk solution diluted with sterile pyrogen-free distilled water to reach a conductivity of about 3.5 to 6.0 millisiemens, after the addition of 10 N HCl to bring the pH to between 6.4-6.6, preferably to pH 6.5.

The fractionation method described involves the passage of the plasma through anionic and cationic resin beds. It is recognized that there are several alternative choices that can accomplish the aim of separating in pure form clinically effective IgG4.

In preferred embodiments, the diluted plasma is passed through a suitable size bed (16-50L) of an anion exchange resin such as DEAE-Sepharose® (CL-6B) which has been equilibrated with 0.025 M sodium phosphate at pH 6.5. The material is pumped through the bed at the rate of about 175 ml/minute. The plasma should then be followed with 0.025M sodium phosphate pH 6.5. The pH 6.5 buffer solution contains 0.653 g $Na_2HPO_4 \cdot H_2O$ and 2.855 g of $NaH_2PO_4 \cdot H_2O$ per liter of distilled water (Pyrogen free) at 25° C. The effluent is preferably monitored for protein content by observing the Absorbance at 280 nM with a suitable instrument, such as the Pharmacia Single Path Monitor UV-1. The effluent can be collected when the UV trace on the recorder indicates a sharp rise in absorbency, and collection is continued until the absorbency drops to about 5% of the peak value.

The effluent is maintained at about pH 6.5, and is passed directly through a similarly prepared, but about one third the column volume, of a suitable cation exchange resin, such as CM-Sepharose® (CL6B) that has been equilibrated to pH 6.5 with 0.025 M sodium phosphate buffer as above. The material is pumped through the column as before, at about 175 ml/minute. The protein solution should then be followed with 0.025 M sodium phosphate at pH 6.5.

The effluent is then monitored as before at 280 nM with a suitable instrument, and the effluent should begin to be collected when the UV trace on the recorder indicates a sharp rise in absorbency. Collection should be continued until the absorbency drops to about 5% of the peak value. This effluent is mostly, if not entirely, IgG4. The resin beds as well as the buffer solutions and collecting vessels should be pyrogen-free and sterilized by autoclaving.

In certain embodiments, the IgG4 containing effluent is further processed into other pharmaceutical compositions. For example, sodium chloride (sterilized and pyrogen-free) can be added to the effluent to final level of about 0.03 to about 0.05M, and the effluent immune globulin is concentrated, preferably by ultrafiltration with a suitable apparatus, such as the Millipore Cassette System with a 10,000 nominal molecular weight cut-off membrane (PTGC 000 05 ca No). The filtration rate is about 425 ml/minute and the approximate inlet and outlet pressures are 16 psi and 10 psi respectively. When the starting volume has been reduced about 70-fold, the cassette is flushed with about 300-500 ml of 0.05M sodium chloride solution, and this is added to the immune globulin concentrate. The solution is then frozen and maintained at −30° C. or lower. The solution is then thawed, and sufficient sterile and pyrogen-free lactose is added to the bulk solution to result in a solution of about 0.25 to 0.35 osmolar. The concentrated immune globulin is then sterile filtered through a 0.22 micron membrane filter, and stored at about −10° C. or colder until vialing and lyophilization.

The sample is then thawed at about 5° C., and filtered through a 0.02 micron filter to decrease bacteria and viral contamination. Samples are removed for tests of sterility, pyrogenicity and potency. Following successful testing, the vials are filled aseptically at a specified fill volume of bulk solution. The vials are subjected to a standard freeze-dry cycle, and the chamber is restored to atmospheric pressure with sterile nitrogen. The freeze-drying cycle is dependent on the apparatus used or the vendor used if this work is sub-contracted.

Samples are obtained for moisture determination during drying of the product at full vacuum at the terminal drying temperature. After acceptable moisture results have been obtained, the chamber should be restored to atmospheric pressure with sterile nitrogen. Within the lyophilizer, the freeze-dried vials should be aseptically stoppered and sealed.

III. Pharmaceutical Compositions

Accordingly, in certain aspects, the present invention provides pharmaceutical compositions comprising a pharmaceutically acceptable carrier or excipient and an antibody preparation (e.g., IgG4 that is substantially free of other IgG subtypes, IgG1 that is substantially free of other IgG subtypes, IgG2 that is substantially free of other IgG subtypes, IgG3 that is substantially free of other IgG subtypes, and combinations thereof).

For preparing pharmaceutical compositions from the active components of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component. In tablets, the active component is mixed with the carrier having the necessary binding properties in suitable proportions and compacted in the shape and size desired.

The powders and tablets preferably contain from 1% or 5% or 10% to 70% (w/w) of the active component. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active component with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.01 mg to 1000 mg, preferably 1.0 mg to 100 mg according to the particular application and the potency of the active component.

IV. Methods of Treatment

In therapeutic applications, the active components of the present invention can be prepared and administered in a wide variety of oral and parenteral dosage forms. Thus, the active components of the present invention can be administered by injection, that is, intravenously, intramuscularly, intracutaneously, subcutaneously, or intraperitoneally. Also, the active components described herein can be administered by inhalation, for example, intranasally. Additionally, the active components of the present invention can be administered transdermally.

In preferred embodiments, the active components utilized in the pharmaceutical method of the invention are administered every four months at 50-1000 mg/dose, repeated once. Thus, each patient in certain embodiments would receive at least two doses per year. The dosages, however, may be varied depending upon the requirements of the patient, the severity of the condition being treated, and the active component being employed. Determination of the proper dosage for a particular situation is within the skill of the practitioner. Typically, the host or subject in each of these methods is human, although other animals can also benefit from the foregoing treatments.

The pharmaceutical compositions of the present invention can be administered in an acute (i.e., at the time of need) or in a prophylactic manner (i.e., before a condition or disease is manifested; before exposure to an allergen or antigen). The compositions can be used to treat a variety of type I allergies depending what antigen(s) the particular antibodies are directed against. Allergies to materials such as bee venom, stinging insect venoms, hymenoptera venoms, snake venoms, reptile venoms, ragweed, Spring allergens, House allergens can be acutely or prophylactically treated using the antibody compositions of the present invention.

In other embodiments, the pharmaceutical compositions of the present invention can be used to desensitize a patient to an allergen or antigen. For example, certain patients can be desensitized to the venom of an insect by first administering an immune globulin preparation (e.g., IgG4 that is essentially free from other IgG subtypes) and then administering the venom of the insect in a desensitizing amount. In these patients, the amount of blocking antibody in their serum levels off, suggesting that the patient is producing their own blocking antibodies against one or more bee venom antigens.

EXAMPLES

The following examples are offered to illustrate, but not to limit the claimed invention.

Example 1

A liter of clarified plasma from bee keepers diluted with 3 parts of distilled water (containing about 10 g of IgG) was applied to a DEAE-Sepharose® column equilibrated with 0.025 M sodium phosphate at pH 6.5. The column is developed with 0.025 M sodium phosphate at pH 6.5. The flow-through fractions containing 9 g of IgG were then applied to a CM-Sephadex® column equilibrated in 0.025 M sodium phosphate at pH 6.5. The CM-Sephadex® column was then developed with 0.025 M sodium phosphate at pH 6.5. The flow-through fractions containing 405 mg of IgG4 were pooled and analyzed using SDS-PAGE. The IgG4 sample was electrophoresed on the same gel as a a sample of IgG purified using the Cohn method (see U.S. Pat. No. 2,390,074; and Cohn et al., (1946) *JACS* 68:459-475, 1946). While the Cohn method produced a heterogenous mix of IgGs and degraded protein, the method of the present invention produced a single band migrating at the appropriate molecular weight, with no visible signs of protein degradation.

Using sub-type specific ELISA, the sample was determined to be greater than 98% of IgG4 by ELISA, and contained less than 3% of IgG1, IgG2 or IgG3.

The specificity of the IgG4 blocking antibody was analyzed by ELISA and found to contain the following percentage of blocking antibody against the following bee venom antigens:

| Percentage of Blocking Antibody | Antigen |
|---|---|
| 68% | Phospholipase A2 |
| 18% | Melittin |
| 10% | Hyaluronidase |
| 4% | Acid Phosphatase |

Example 2

A study was performed to determine if IgG4 (purified using the method of example 1) could block immune responses to a bee venom injection. This small study was conducted under the aegis of the Scripps Regional Institutional Review Board, which is now responsible for Human Clinical Trial Oversight for all of San Diego County.

The purified IgG4 was purified from plasma donated by beekeepers who were entirely immune to the stings of bees and whose blood serum contained high levels of IgG blocking-antibody as determined by the Basophil Histamine Release (BHR) (Haydik and Ma, (1998) *Clin. Rev. Allergy* Summer;6(2):141-162) and other tests.

The human patient volunteers were shown, by the injection of minute amounts of bee venom, BHR and other laboratory blood tests, to be exquisitely and dangerously allergic to bee venom. After a three-week waiting period, each patient was administered selected and pooled purified IgG4 followed by repeated skin testing (with venom equivalent to about two bee stings) and careful laboratory studies to determine their post-infusion allergy status. These tests were continued until their allergy began to reappear. Each patient was their own control in that before treatment they were very allergic, while the antibody was in their blood they were resistant to bee stings, and when the antibody disappeared, their allergy returned.

Figure 1:
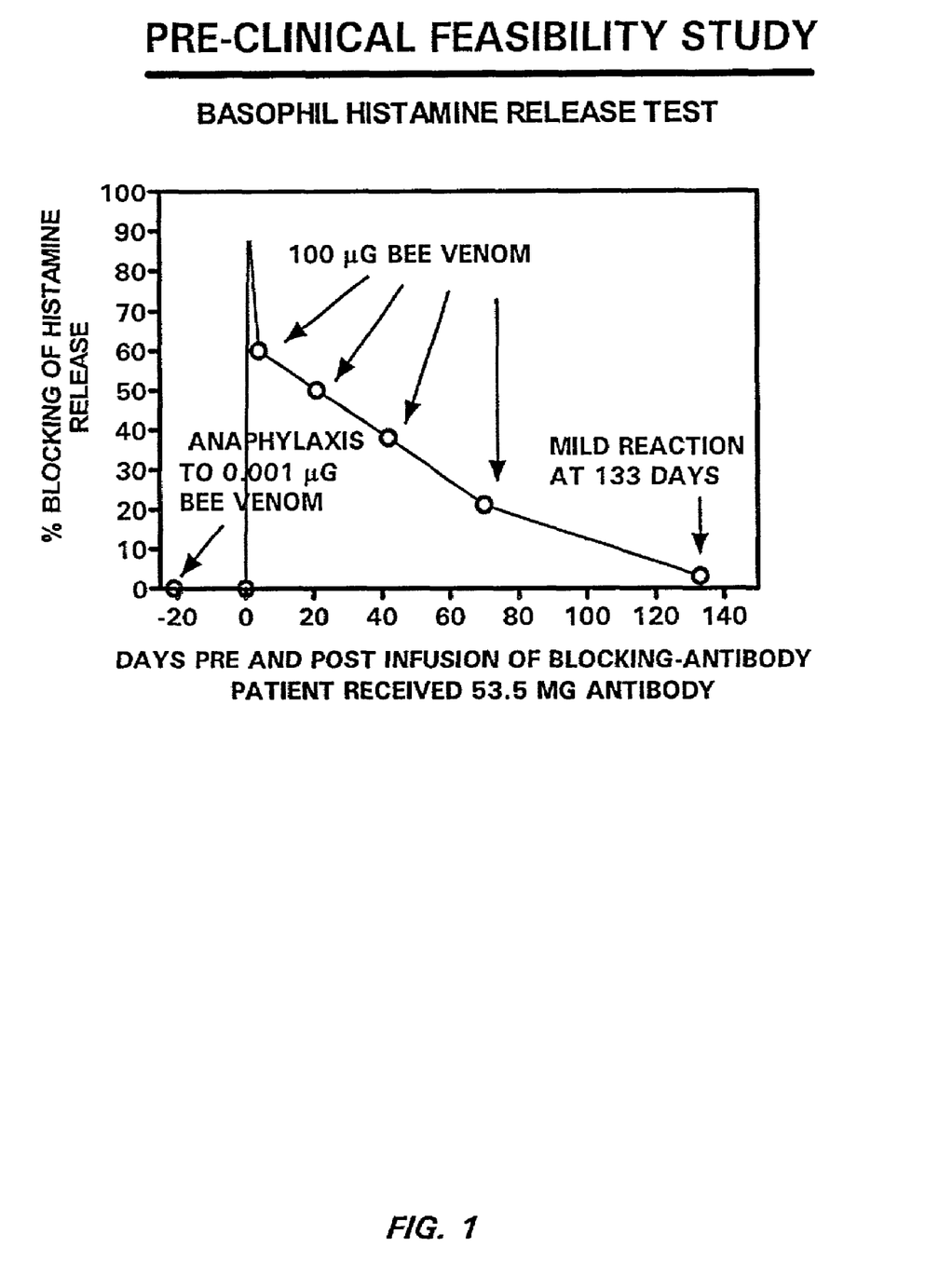
FIG. 1 illustrates that the basophil histamine release of a representative bee sting allergic patient was reduced approximately 95 percent just after injection at Day zero with IgG4 purified from beekeepers. The patient exhibited anaphylaxis to just 0.001 micrograms of bee venom 20 days before the injection with IgG4.No reactions were seen with to 100 micrograms of bee venom in a bee venom skin test after IgG4 administration, until a mild reaction was seen at Day 133 post-injection of IgG4.

The results from a typical highly allergic patient from the study in the combined skin test is displayed in FIG. 1. FIG. 1 is a graph of BHR for a typical bee sting allergic patient before and after injection with IgG4 purified as in Example 1. FIG. 1 shows the successful control of the patient's allergy to bee venom while the blocking-antibody persists in the patient. This BHR graph shows the percentage of the histamine blocking by the patient's IgG4. The blocking-antibody, administered on day zero, shows the steep increase in blocking protection which peaks in the plasma at about 95% and within 4 days has reduced to 60% as the antibody leaves the blood stream and slowly equilibrates with the extravascular space (i.e., lymph, liver, spleen, etc). The antibody-specific immunoglobulin was slowly catabolized until at the $133^{rd}$ day it had reached a level where the patient again began to experience mild symptoms of anaphylaxis when tested. Arrows show when the tests were performed on the patient. Each test was done with doses of venom equivalent to approximately two bee stings. At day 4,the patient is protected to 15-20 stings.

The success of this example quite clearly demonstrates that the use of blocking immunoglobulin to prevent allergens to bee stings is a general phenomenon that applies to all Type 1 allergies. In the case shown, the patient was able to withstand a dose of bee venom 100,000 times the dose that originally caused anaphylaxis for a period of over 120 days.

Figure 2:
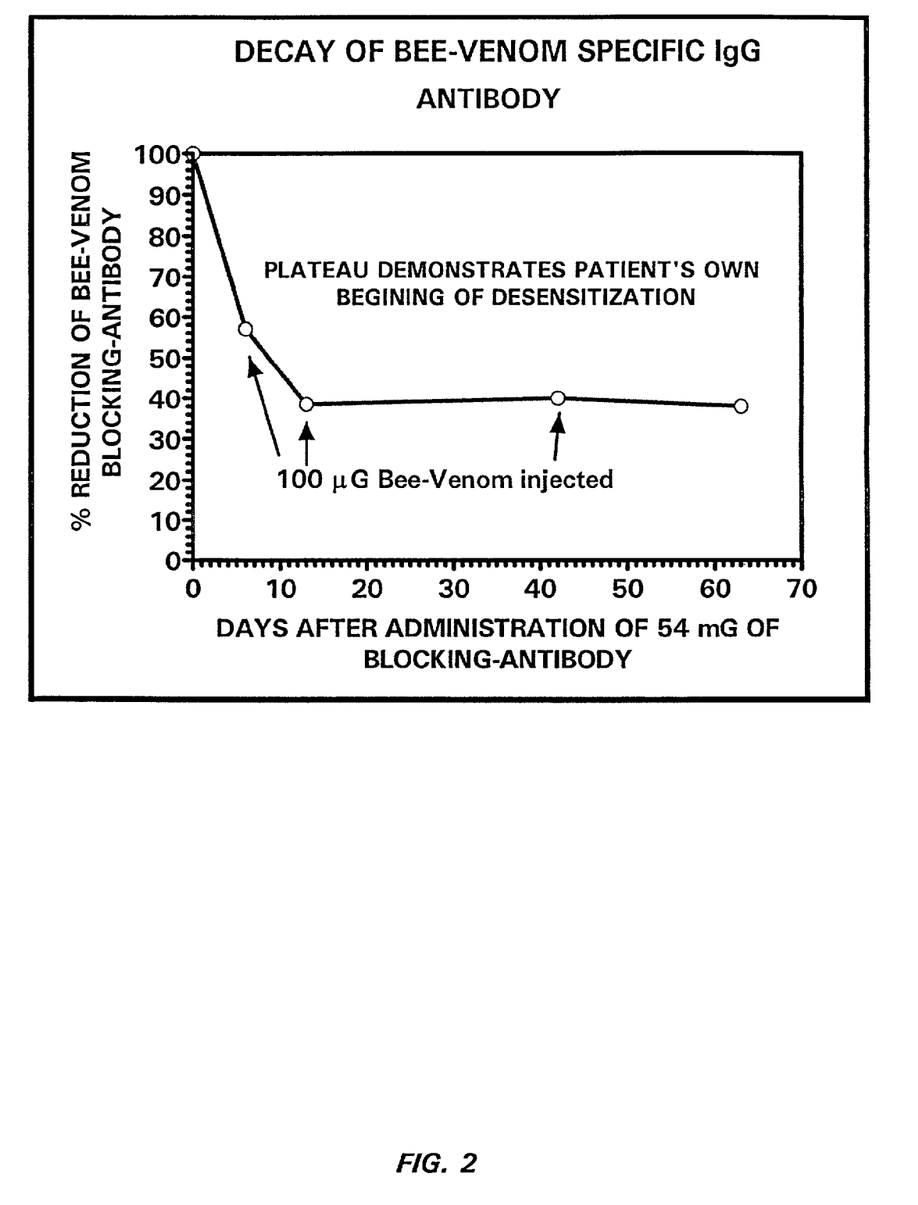
FIG. 2 is a graph of the percent reduction in blocking antibody versus days after injection with IgG4.In approximately 30% of the patients, the amount of blocking antibody in the patients' serum reached a plateau after about 12 days. The results from a representative patient of that subpopulation is displayed in FIG. 2. This graph demonstrates that the reduction in the amount of blocking antibody does not decrease after amount 12 days.

In approximately 30% of the patients, the amount of blocking antibody in their serum reached a plateau after about 12 days (see FIG. 2). This result suggest that the combination of the IgG4 and bee venom can result in the patient generating their own blocking antibody, leading to desensitization of the patient to bee venom.

Example 3

IgG1 was purified by taking the IgG fractions from the DEAE-Sepharose® column of Example 1, and applying the material to a CM-Sephadex® column equilibrated to 0.025M sodium phosphate at pH 6.5. Purified IgG1 was eluted from the CM-Sephadex® column using a shallow pH gradient. The IgG1 likely elutes from the column at a pH that is at or more basic than the pI of IgG1. The IgG1 sample was then analyzed by SDS-PAGE and evidenced a single band migrating at the appropriate molecular weight . Using sub-type specific ELISA, the sample was determined to be greater than 98% of IgG1 by ELISA, and contained less than 2% of IgG2, IgG3 or IgG4.

Example 4

Similar to the method of Example 3,it is possible to purify IgG2 that is essentially free of other IgG subtypes, and to purify IgG3 that is essentially free of other IgG3 subtypes. The IgG containing flow-through fractions of the DEAE column can be applied to a CM-Sephadex® column equilibrated to 0.025M sodium phosphate at pH 6.5. Purified IgG2 and IgG3 can then each be eluted separately using a shallow pH gradient and/or a shallow ionic strength gradient. The IgG2 and IgG3 should elute from the CM-Sephadex® column at a pH that is at or more basic that the pI of the respective subtype.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating a patient envenomated by an insect sting comprising:
   administering a pharmaceutical composition comprising between 50-1000 milligrams of an IgG4 preparation that is essentially free of other IgG subtypes to a patient envenomated by an insect sting, wherein the IgG4 preparation has no visible signs of protein degradation.

2. The method of claim 1, wherein said insect is selected from the group consisting of flying insects, bees, honey bees, Africanized "killer" bees, wasps, hornets, yellow jackets, and hymenoptera.

3. The method of claim 1, wherein said pharmaceutical composition is administered prior to said patient being envenomated.

4. The method of claim 1, wherein said pharmaceutical composition is administered after said patient is envenomated.

5. The method of claim 1, wherein said pharmaceutical composition is administered to the patient by injection.

6. The method of claim 1, wherein said pharmaceutical composition is administered to the patient orally.

7. The method of claim 1, wherein said pharmaceutical composition is administered to the patient by inhalation.

8. The method of claim 1, wherein said pharmaceutical composition is administered to the patient transdermally.

9. The method of claim 1, wherein the IgG4 preparation has less than 3% each of IgG1, and IgG2 subtypes.

10. The method of claim 1, wherein the IgG4 preparation consists essentially of IgG4.

11. A method of treating a patient envenomated by an insect sting comprising:
    administering a pharmaceutical composition comprising a therapeutic amount of an IgG4 preparation that is essentially free of other IgG subtypes to a patient envenomated by an insect sting, wherein the IgG4 preparation has no visible signs of protein degradation and wherein the pharmaceutical composition is administered to the patient at four month intervals.

12. A method of treating a patient envenomated by an insect sting comprising:
    administering a pharmaceutical composition comprising a therapeutic amount of an IgG4 preparation that is essentially free of other IgG subtypes to a patient envenomated by an insect sting, wherein the IgG4 preparation has no visible signs of protein degradation, and wherein, after administration of the pharmaceutical composition, the patient is able to withstand a second dose of bee venom that is 100,000 times larger than a first dose of bee venom that causes anaphylaxis before administration of the pharmaceutical composition.

13. The method of claim 11, or claim 12, wherein the therapeutic amount of IgG4 is 50-1000 milligrams.

14. The method of claim 12, wherein the second dose of bee venom is administered four months after the first dose.

* * * * *